United States Patent
Takakura et al.

(10) Patent No.: US 11,033,559 B2
(45) Date of Patent: Jun. 15, 2021

(54) LEUKOCYTE INFILTRATION PROMOTING AGENT AND ANTITUMOR IMMUNOSTIMULATORY AGENT

(71) Applicant: OSAKA UNIVERSITY, Osaka (JP)

(72) Inventors: Nobuyuki Takakura, Osaka (JP); Hisamichi Naito, Osaka (JP); Kazuhiro Takara, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 376 days.

(21) Appl. No.: 15/762,644

(22) PCT Filed: Sep. 29, 2016

(86) PCT No.: PCT/JP2016/078941
§ 371 (c)(1),
(2) Date: Mar. 23, 2018

(87) PCT Pub. No.: WO2017/057643
PCT Pub. Date: Apr. 6, 2017

(65) Prior Publication Data
US 2018/0264015 A1 Sep. 20, 2018

(30) Foreign Application Priority Data
Sep. 29, 2015 (JP) .............................. JP2015-191202

(51) Int. Cl.
| | | |
|---|---|---|
| *A61K 31/662* | (2006.01) | |
| *A61K 31/685* | (2006.01) | |
| *A61P 35/00* | (2006.01) | |
| *A61P 37/04* | (2006.01) | |
| *A61K 45/00* | (2006.01) | |
| *A61K 31/683* | (2006.01) | |
| *A61K 35/17* | (2015.01) | |
| *A61K 38/00* | (2006.01) | |
| *A61K 39/395* | (2006.01) | |

(52) U.S. Cl.
CPC .......... *A61K 31/662* (2013.01); *A61K 31/683* (2013.01); *A61K 31/685* (2013.01); *A61K 35/17* (2013.01); *A61K 38/005* (2013.01); *A61K 39/39558* (2013.01); *A61K 45/00* (2013.01); *A61K 45/05* (2013.01); *A61P 35/00* (2018.01); *A61P 37/04* (2018.01)

(58) Field of Classification Search
None
See application file for complete search history.

(56) References Cited

U.S. PATENT DOCUMENTS

| | | | |
|---|---|---|---|
| 4,372,949 A | 2/1983 | Kodama et al. | |
| 5,260,288 A | 11/1993 | Igarashi et al. | |
| 5,565,439 A | 10/1996 | Piazza et al. | |
| 10,071,051 B2 * | 9/2018 | Okubo | A61K 31/437 |
| 2003/0036531 A1 | 2/2003 | Paha et al. | |
| 2005/0054095 A1 | 3/2005 | Andre | |
| 2014/0220057 A1 * | 8/2014 | Okubo | A61K 31/716 424/185.1 |
| 2017/0112861 A1 | 4/2017 | Takakura et al. | |

FOREIGN PATENT DOCUMENTS

| | | |
|---|---|---|
| JP | 58-105922 | 6/1983 |
| JP | 63-152327 | 6/1988 |
| JP | 8-500816 | 1/1996 |
| JP | 2005-530488 | 10/2005 |
| WO | 02/072082 | 9/2002 |
| WO | 2012/049647 | 4/2012 |
| WO | 2015/152412 | 10/2015 |

OTHER PUBLICATIONS

Blaho et al. 2014 J. Lipid Res. 55: 1596-1608.*
Chu et al. 2015 Int J Clin Exp Med; 8(10): 17117-17122.*
Drzazga et al. 2014 Acta Poloniae Pharmaceutica—Drug Research 71: 887-899.*
Federico et al. 2016 J. Lipid Res. 57: 25-35.*
Gotoh et al. 2012 Biochem. Soc. Trans. 40: 31-36.*
Kihara et al. 2014 British Journal of Pharmacology 171: 3575-3594.*
Makide et al. 2014 J. Lipid Res. 55: 1986-1995.*
Newton et al. 2015 Experimental Cell Research 333: 195-200.*
Oskeritzian 2015 Molecular Immunology 63: 104-112.*
Proia et al. 2015 J Clin Invest. 125(4): 1379-1387.*
Pyne et al. 2014 Advances in Biological Regulation 54: 121-129.*
Stoddard et al. 2015 Biomolecules and Therapeutics 23(1): 1-11.*
Tabuchi 2015 Lipids in Health and Disease 14: 56 (p. 1-9).*
Tigyi et al. 2010 British Journal of Pharmacology 161: 241-270.*
Uwamizu et al. 2015 J. Biochem. 157(3): 151-160.*
Wong et al. 2010 Assay Drug Dev Technol. 8(4): 459-470.*
Xu et al. 2013 FEBS Journal 280: 5652-5667.*
Yung et al. 2014 J. Lipid Res. 55: 1192-1214.*
Noguchi et al. J Biol. Chem. 2003; 278(28): 25600-25606 (provided by applicant).*
Yanagida et al. Biochim Biophys Acta. 2013; 1831(1): 33-41 (provided by applicant).*
Abby L Parrill, Future Med Chem. 2014; 6(8): 871-883 (provided by applicant).*
Kiss et al. Mol Pharmacol. 2012; 82(6): 1162-1173 (provided by applicant).*

(Continued)

*Primary Examiner* — Ilia I Ouspenski
(74) *Attorney, Agent, or Firm* — Wenderoth, Lind & Ponack, L.L.P.

(57) ABSTRACT

A lysophospholipid receptor-activating substance is able to normalize abnormal blood vessels in tumors without affecting normal blood vessels and to thus induce or promote infiltration of leukocytes into the whole or partial region of a tumor. Therefore, such a lysophospholipid receptor-activating substance is useful as a leukocyte infiltration promoter and an antitumor immunostimulant. Moreover, such a lysophospholipid receptor-activating substance can enhance cancer immunotherapy when used in combination with cancer immunotherapy, and is therefore useful as an agent for enhancing cancer immunotherapy.

13 Claims, 6 Drawing Sheets

(56) References Cited

OTHER PUBLICATIONS

Takara et al., Cell Reports, 2017, vol. 20, pp. 2072-2086 (provided by applicant).*
Eino et al., Cancer Res., 2018, vol. 78, No. 23, pp. 6607-6620 (provided by applicant).*
Extended European Search Report dated Apr. 29, 2019 in corresponding European Patent Application No. 16851814.0.
Office Action dated May 2, 2019 in corresponding Australian Patent Application No. 2016329670.
Kim et al., "Angiogenesis promoter containing sphingosine 1-phosphate as active ingredient", WPI/2017 Clarivate Analytics, vol. 2001, No. 51, 2001, 1 page.
Qi et al., "Sustained delivery of sphingosine 1-phosphate using poly(lactic-co-glycolic acid)-based microparticles stimulates Akt/ERK-eNOS mediated angiogenesis and vascular maturation restoring blood flow in ischemic limbs of mice", European Journal of Pharmacology, 2010, vol. 634, No. 1-3, pp. 121-131.
International Search Report dated Dec. 20, 2016 in International Application No. PCT/JP2016/078941.
Folkman J, et al, "Isolation of a tumor factor responsible for angiogenesis", J Exp Med, 1971, vol. 133, pp. 275-288.
Gerber HP, Ferrara N, "Pharmacology and pharmacodynamics of bevacizumab as monotherapy or in combination with cytotoxic therapy in preclinical studies", Cancer Res, 2005, vol. 65, pp. 671-680.
Jain RK, "Normalization of tumor vasculature: An emerging concept in antiangiogenic therapy", Science, 2005, vol. 307, pp. 58-62.
Kidoya H et al, "The apelin/APJ system induces maturation of the tumor vasculature and improves the efficiency of immune therapy", Oncogene 31: 3254-3264, 2012.
Satoh N et al. "Angiopoietin-1 alters tumor growth by stabilizing blood vessels or by promoting angiogenesis", Cancer Sci. vol. 99, No. 12, 2373-2379, 2008.
Maes H et al, "Tumor Vessel Normalization by Chloroquine Independent of Autophagy", Cancer Cell 26, 190-206, Aug. 11, 2014.
Wong PP et al, "Dual-Action Combination Therapy Enhances Angiogenesis while Reducing Tumor Growth and Spread", Cancer Cell 27, 123-137, Jan. 2015.
International Preliminary Report on Patentability dated Mar. 29, 2018 in International Application No. PCT/JP2016/078941.

* cited by examiner

Control group

LPA group

Control group

S1P group

Control group

LPA group

Fig. 4A
Control group
Fig. 4B
LPA group
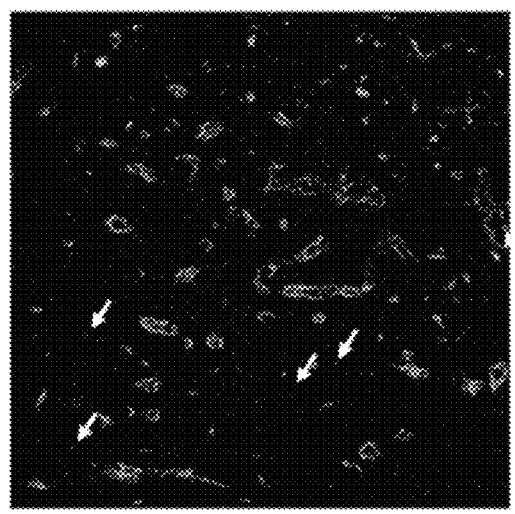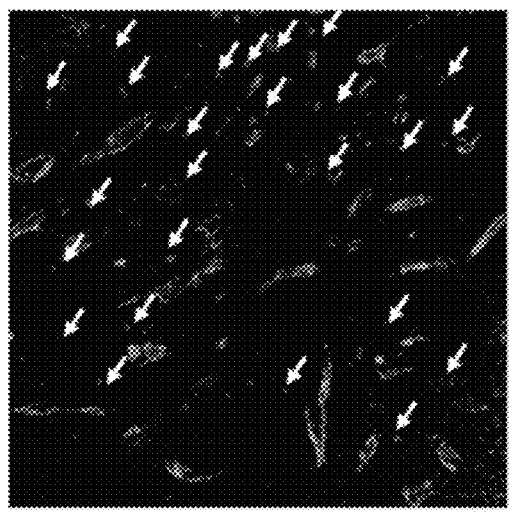
Green: CD31, Red dots (arrows): doxorubicin

LEUKOCYTE INFILTRATION PROMOTING AGENT AND ANTITUMOR IMMUNOSTIMULATORY AGENT

TECHNICAL FIELD

The present invention relates to a leukocyte infiltration promoting agent and an antitumor immunostimulatory agent, and more particularly to a leukocyte infiltration promoting agent and an antitumor immunostimulatory agent each comprising a lysophospholipid receptor-activating substance as an active ingredient.

BACKGROUND ART

The formation of new blood vessels in normal tissue undergoes the process of vasculogenesis to establish a new circulation network. Vasculogenesis includes the steps of development of vascular endothelial cells, assembly of the endothelial cells into tubular structures (tubulogenesis), and vascular maturation by mural cell coverage of the endothelial cells. On the other hand, inflammation- or hypoxia-induced formation of new blood vessels from preexisting blood vessels undergoes the process of angiogenesis (sprouting blood vessel formation). The formation of new blood vessels in tumors also undergoes the process of angiogenesis. Such tumor neovascularization makes it possible to supply tumor cells with oxygen and nutrients. Therefore, focusing on tumor angiogenesis inhibition, antitumor therapies for inhibiting tumor growth have been developed.

In 1971, a factor secreted by tumors was found to induce the formation of new tumor blood vessels from preexisting blood vessels (Non Patent Literature 1), and this angiogenic factor was identified as a vascular endothelial growth factor (VEGF). VEGF plays a role in vascular endothelial cell growth and tubulogenesis by activating VEGF receptors expressed in vascular endothelial cells (VEGFR1, 2, 3), in particular VEGFR2. The first developed anti-VEGF drug is an anti-VEGF neutralizing antibody, and this antibody has been clinically used early on as an angiogenesis inhibitor (Non Patent Literature 2). However, it has been proven that the anti-VEGF neutralizing antibody and VEGF receptor tyrosine kinase inhibitors, which are a different type of angiogenesis inhibitor developed after the anti-VEGF neutralizing antibody, do not produce antitumor effect when used alone. In clinical settings, a combined use of such an angiogenesis inhibitor and an anticancer drug has been shown to produce a superior effect as compared with that of the use of the anticancer drug alone. Recent basic medical studies have indicated that the therapeutic effect of the combined use of the angiogenesis inhibitor and the anticancer drug is attributed to partial normalization of tumor blood vessels by the angiogenesis inhibitor and thus improvement of the delivery of the anticancer drug into tumors (Non Patent Literature 3).

The lumina of normal blood vessels are structurally stabilized by adhesion of mural cells to vascular endothelial cells. Individual vascular endothelial cells tightly adhere to each other via various adhesion molecules, including VE-cadherin, claudin 5, integrins, and connexins, and this structure contributes to the control of the passage of substances and cells from the blood vessels to prevent their leakage. Further, adherens junctions are formed between vascular endothelial cells and mural cells and serve to control vascular permeability by limited molecular transport between vascular endothelial cells and mural cells. Normal blood vessels run parallel to one another. On the other hand, tumor blood vessels have various abnormalities. For example, blood vessels in tumors are hyperpermeable, tortuos, dilated, partially saccular and irregularly branched. Vascular endothelial cells of such blood vessels are also morphologically abnormal, and mural cells for covering vascular endothelial cells are highly interspersed and weakly adhere to vascular endothelial cells in the central part of a tumor. In most part of the tumor blood vessels, such mural cell coverage is absent. These abnormalities are mainly caused by over-secretion of VEGF in tumors.

VEGF is a potent growth factor for vascular endothelial cells and serves to inhibit cell-cell adhesion in vascular endothelial cells, thereby increasing vascular permeability. When such an increased vascular permeability continues, serum components and fibroblasts accumulate in the deep part of a tumor and then the interstitial pressure therein significantly increases. As a result, the internal pressure in blood vessels becomes equal to the tissue pressure in the deep part of the tumor, and this condition impedes the delivery of drugs and the like from blood vessels to tumor tissue. This state is reversed by blocking the intracellular signaling of VEGF. That is, once the intracellular signaling of VEGF is blocked, cell-cell adhesion in vascular endothelial cells is restored, increased vascular permeability returns to normal, and the internal pressure in blood vessels becomes higher than the tissue pressure in the deep part of the tumor, thus providing an environment allowing the delivery of anticancer drugs from blood vessels to tumor tissue. Therefore, a combined use of an angiogenesis inhibitor and an anticancer drug is expected to produce a superior effect as compared with that of the use of the anticancer drug alone.

Based on this hypothesis, the normalization of vascular permeability in tumors for induction of drug delivery to the tumors is now considered to be a potentially effective approach to cancer therapy. On the other hand, there is a concern that angiogenesis inhibitors inhibit the survival of vascular endothelial cells and induce the death of vascular endothelial cells and their interacting vascular mural cells, thereby aggravating ischemia in tumors. Hypoxia in tumors is considered to cause malignant transformation of cancer cells and facilitate cancer invasion and metastasis. Also reported is that angiogenesis inhibitors damage blood vessels in normal tissue and cause severe adverse effects, such as hypertension, lung hemorrhage and renal dysfunction. Under such circumstances, there has been a demand for the development of a drug that normalizes the vascular permeability in tumors without causing the regression of tumor blood vessels and without affecting normal blood vessels.

CITATION LIST

Non Patent Literature

Non Patent Literature 1:
Folkman J, et al.: Isolation of a tumor factor responsible for angiogenesis. J Exp Med 133: 275-288, 1971
Non Patent Literature 2:
Gerber HbP, Ferrara N. Pharmacology and pharmacodynamics of bevacizumab as monotherapy or in combination with cytotoxic therapy in preclinical studies. Cancer Res 65; 671-680, 2005
Non Patent Literature 3:
Jain R K: Normalization of tumor vasculature: An emerging concept in antiangiogenic therapy. Science 307: 58-62, 2005

SUMMARY OF INVENTION

Technical Problem

An object of the present invention is to find a substance that normalizes abnormal blood vessels in tumors without affecting normal blood vessels and to provide a novel application of such a substance.

Solution to Problem

The present invention includes the following to achieve the above-mentioned object.

(1) An agent for enhancing cancer immunotherapy, comprising a lysophospholipid receptor-activating substance as an active ingredient, the agent being capable of inducing or promoting infiltration of leukocytes into the whole or partial region of a tumor, the agent being used in combination with cancer immunotherapy.

(2) The agent for enhancing cancer immunotherapy according to the above (1), wherein the lysophospholipid receptor-activating substance is a lysophospholipid, a precursor thereof, or a derivative of the lysophospholipid or the precursor.

(3) The agent for enhancing cancer immunotherapy according to the above (1) or (2), wherein the lysophospholipid receptor is a lysophosphatidic acid receptor.

(4) A leukocyte infiltration promoting agent comprising a lysophospholipid receptor-activating substance as an active ingredient, the agent being capable of inducing or promoting infiltration of leukocytes into the whole or partial region of a tumor.

(5) The leukocyte infiltration promoting agent according to the above (4), wherein the leukocytes are CD4-positive cells and/or CD8-positive cells.

(6) The leukocyte infiltration promoting agent according to the above (4) or (5), wherein the lysophospholipid receptor-activating substance is a lysophospholipid, a precursor thereof, or a derivative of the lysophospholipid or the precursor.

(7) The leukocyte infiltration promoting agent according to any one of the above (4) to (6), wherein the lysophospholipid receptor is a receptor for a lysophospholipid selected from the group consisting of lysophosphatidic acid, lysophosphatidylserine, lysophosphatidylcholine, lysophosphatidylethanolamine, lysophosphatidylinositol, lysophosphatidylglycerol, sphingosine-1-phosphate, sphingosyl phosphorylcholine and platelet-activating factor (PAF).

(8) The leukocyte infiltration promoting agent according to the above (7), wherein the lysophospholipid receptor is a lysophosphatidic acid receptor.

(9) The leukocyte infiltration promoting agent according to any one of the above (4) to (8), wherein the agent is used in combination with cancer immunotherapy.

(10) The leukocyte infiltration promoting agent according to the above (9), wherein the cancer immunotherapy is a therapy for reversal of immunosuppression.

(11) An antitumor immunostimulatory agent comprising a lysophospholipid receptor-activating substance as an active ingredient, the agent being capable of inducing or promoting infiltration of leukocytes into the whole or partial region of a tumor.

(12) The antitumor immunostimulatory agent according to the above (11), wherein the leukocytes are CD4-positive cells and/or CD8-positive cells.

(13) The antitumor immunostimulatory agent according to the above (11) or (12), wherein the lysophospholipid receptor-activating substance is a lysophospholipid, a precursor thereof, or a derivative of the lysophospholipid or the precursor.

(14) The antitumor immunostimulatory agent according to any one of the above (11) to (13), wherein the lysophospholipid receptor is a receptor for a lysophospholipid selected from the group consisting of lysophosphatidic acid, lysophosphatidylserine, lysophosphatidylcholine, lysophosphatidylethanolamine, lysophosphatidylinositol, lysophosphatidylglycerol, sphingosine-1-phosphate, sphingosyl phosphorylcholine and platelet-activating factor (PAF).

(15) The antitumor immunostimulatory agent according to the above (14), wherein the lysophospholipid receptor is a lysophosphatidic acid receptor.

Advantageous Effects of Invention

The lysophospholipid receptor-activating substance contained as an active ingredient in the agent for enhancing cancer immunotherapy, the leukocyte infiltration promoting agent and the antitumor immunostimulatory agent of the present invention is able to normalize or substantially normalize abnormal blood vessels in tumors with no or minimal influence on normal blood vessels. Due to these effects, the lysophospholipid receptor-activating substance enables the induction or promotion of infiltration of leukocytes into the whole or partial region of a tumor and the stimulation of antitumor immunity in the tumor, leading to the inhibition of tumor growth. The agent for enhancing cancer immunotherapy, the leukocyte infiltration promoting agent and the antitumor immunostimulatory agent of the present invention do not destroy or minimally destroy tumor vessels and do not induce hypoxia in tumors. For these reasons, they have an advantage of not inducing malignant transformation of cancer cells. Further, when used in combination with cancer immunotherapy, such as cancer vaccine therapy, immune cell infusion therapy (e.g., chimeric antigen receptor-modified T-cell therapy etc.) and a therapy for reversal of immunosuppression (e.g., immune checkpoint inhibition therapy etc.), the agent for enhancing cancer immunotherapy, the leukocyte infiltration promoting agent and the antitumor immunostimulatory agent of the present invention can enhance the cancer immunotherapy and its antitumor activity.

BRIEF DESCRIPTION OF DRAWINGS

FIG. 1A shows the results for the control group and FIG. 1B shows the results for the LPA group.

FIG. 2A shows the results for the control group and FIG. 2B shows the results for the S1P group.

FIG. 3A shows the results for the control group and FIG. 3B shows the results for the LPA group.

FIGS. 4A and 4B show drug delivery from tumor blood vessels to tumor tissues in LLC tumor-bearing mice after administration of lysophosphatidic acid (LPA) and doxorubicin. FIG. 4A shows the results for the control group and FIG. 4B shows the results for the LPA group.

DESCRIPTION OF EMBODIMENTS

Figure 1A:
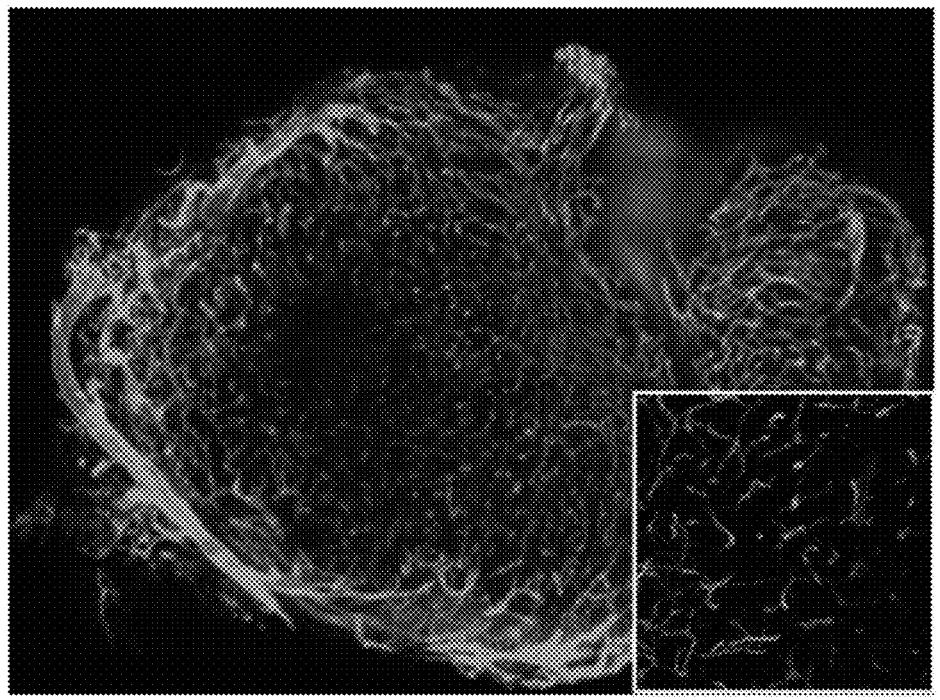
FIGS. 1A and 1B show the structural changes in tumor blood vessels in Lewis lung cancer (LLC) tumor-bearing mice after administration of lysophosphatidic acid (LPA) or an LPA derivative, VPC31144S.

Lysophospholipids are a family member of phospholipids having one acyl group. Lysophospholipids are classified into two classes: one with a glycerol backbone and the other with a sphingosine backbone. Each class includes a large number of molecular species with different combinations of a polar group and an acyl group bound to the backbone. Lysophospholipids are known as a lipid mediator that exhibits various biological activities by binding to a specific receptor. However, little was known about the physiological functions of lysophospholipids in a living body. In particular, nothing was known about their effects on blood vessels in tumors.

The present inventors administered lysophosphatidic acid (LPA), a member of the lysophospholipid family, to tumor-bearing mice generated by subcutaneous inoculation of cancer cells. As a result, tumor blood vessels, which had been tortuous and irregularly branched before administration, formed a network as observed in normal tissue. In addition, the irregular luminal surface of tumor blood vessels before LPA administration became smooth after LPA administration. Further, the excessively increased vascular permeability of tumor blood vessels was reversed to the normal level by LPA administration. That is, the present inventors found that LPA exhibits the following three effects in solid cancer: inducing vascular network formation, thereby normalizing blood vessels; inducing the formation of a smooth vascular lumen; and normalizing vascular permeability. To advance the research, the present inventors examined the localization of immune cells in a tumor after the normalization of blood vessels by LPA. As a result, in LPA-treated mice, a larger number of CD4-positive cells and CD8-positive cells were present in the whole region of the tumor including the central part of the tumor as compared with the tumor tissue in non-treated mice. That is, the present inventors found that LPA is capable of inducing or promoting infiltration of immune cells into the whole region of a tumor.

Increased infiltration of CD8-positive cytotoxic T cells and CD4-positive helper T cells into a tumor is expected to result in the stimulation of antitumor immunity and of cytotoxic T-cell attack on tumor cells, leading to the induction of antitumor effect. Based on this hypothesis, the present inventors administered LPA or a known anticancer drug, 5-FU, to subcutaneous tumor-bearing mice (cancer-bearing mice) and examined tumor growth. As a result, it was found that LPA has an inhibitory effect on tumor growth as with 5-FU. That is, the present inventors found that LPA induces or promotes infiltration of immune cells into the whole region of a tumor and thus stimulates antitumor immunity in the tumor.

The receptor for LPA (LPAR) is known to have six subtypes, namely, LPAR1 to LPAR6. LPAR1 to LPAR3 are reportedly highly expressed in cancer cells, and in in vitro culture, cancer cell growth is induced by lysophosphatidic acid. In previous studies, the present inventors analyzed LPAR expression in vascular endothelial cells in tumor tissue in mice, and confirmed the expression of LPAR1, LPAR4 and LPAR6 in the cells. Further, the present inventors found that cell-cell adhesion is irregular in LPAR4-knockdown vascular endothelial cells, that is, at least LPAR4 mediates the normalization of tumor vessels (PCT/JP2015/060666).

Therefore, specifically activating LPARs that are specifically expressed in tumor vascular endothelial cells and involved in the normalization of blood vessels, except for LPAR1 to LPAR3, which are highly expressed in cancer cells, can achieve cancer treatment without stimulating cancer cell growth or mobility. That is, LPA receptor agonists capable of specifically activating LPAR4 are potentially as useful as lysophospholipids to serve as an active ingredient in leukocyte infiltration promoting agents and antitumor immunostimulatory agents. Moreover, lysophospholipid receptor agonists capable of inducing the normalization of blood vessels, including agonists of as-yet-identified lysophospholipid receptors, are potentially useful as an active ingredient in leukocyte infiltration promoting agents and antitumor immunostimulatory agents. The term "normalization of blood vessels" means that vascular permeability and abnormal vascular network come closer to normal and are not necessarily required to become completely normal.

The present invention provides a leukocyte infiltration promoting agent comprising a lysophospholipid receptor-activating substance as an active ingredient, the agent being capable of inducing or promoting infiltration of leukocytes into the whole or partial region of a tumor. The present invention also provides an antitumor immunostimulatory agent comprising a lysophospholipid receptor-activating substance as an active ingredient, the agent being capable of inducing or promoting infiltration of leukocytes into the whole or partial region of a tumor. The present invention also provides an agent for enhancing cancer immunotherapy, comprising a lysophospholipid receptor-activating substance as an active ingredient, the agent being capable of inducing or promoting infiltration of leukocytes into the whole or partial region of a tumor. Hereinafter, those embodiments of the present invention are collectively referred to as "the agent of the present invention."

The lysophospholipid receptor to be activated by the active ingredient of the agent of the present invention is not particularly limited and may be a known lysophospholipid receptor or an as-yet-discovered lysophospholipid receptor. The lysophospholipid receptor is, for example, a receptor for a lysophospholipid selected from the group consisting of lysophosphatidic acid (LPA), lysophosphatidylserine (LPS), lysophosphatidylcholine (LPC), lysophosphatidylethanolamine (LPE), lysophosphatidylinositol (LPI), lysophosphatidylglycerol (LPG), sphingosine-1-phosphate (S1P), sphingosyl phosphorylcholine (SPC) and platelet-activating factor (PAF). In some embodiments, the lysophospholipid receptor may be a lysophosphatidic acid receptor (LPAR), a lysophosphatidylcholine receptor (LPCR) or a sphingosine-1-phosphate receptor (S1PR). In some embodiments, the lysophospholipid receptor may be a lysophosphatidic acid receptor (LPAR). In some embodiments, the lysophospholipid receptor may be a lysophospholipid receptor expressed in vascular endothelial cells or a lysophospholipid receptor specifically expressed in vascular endothelial cells. The lysophospholipid receptor specifically expressed in vascular endothelial cells may be, for example, a human LPAR corresponding to a mouse LPAR4.

The lysophospholipid receptor-activating substance is not limited to lysophospholipids, and lysophospholipid derivatives, lysophospholipid precursors and derivatives thereof can be used as an active ingredient. In addition to these examples, other lysophospholipid receptor agonists (e.g., low molecular weight compounds, nucleic acids, peptides, proteins, antibodies, etc.) can also be used as an active ingredient. Known lysophospholipid receptor agonists include, for example, the LPA4 receptor agonists described in Wong et al. (Assay Drug Dev Technol. 2010 August; 8(4):459-70. doi:10.1089/adt.2009.0261.). In some embodiments, the lysophospholipid receptor-activating substance may be a lysophospholipid, a lysophospholipid precursor or a derivative thereof.

Examples of the lysophospholipid include LPA, LPS, LPC, LPE, LPI, LPG, S1P, SPC and PAF as described above. The lysophospholipid is not limited to these examples, and other lysophospholipids can be used as the lysophospholipid receptor-activating substance. In some embodiments, the lysophospholipid may be LPA, LPC or S1P. In some embodiments, the lysophospholipid may be LPA. As the active ingredient of the agent of the present invention, one type of lysophospholipid maybe used, and two or more types of lysophospholipids may be used in combination. The acyl group of the lysophospholipid is not particularly limited. In some embodiments, the acyl group of the lysophospholipid may be an acyl group of 16 to 22 carbon atoms with a degree of unsaturation of 0 to 6, and more particularly, the ratio of the number of carbon atoms to the degree of unsaturation in the acyl group may be 16:1, 18:1, 18:2, 18:3, 20:1, 20:2, 20:3, 20:4, 20:5, 22:1, 22:2, 22:3, 22:4, 22:5 or 22:6. The lysophospholipid may be a 1-acyl lysophospholipid or a 2-acyl lysophospholipid. In some embodiments, the lysophospholipid may be a 1-acyl lysophospholipid.

Examples of the lysophospholipid precursor include phosphatidic acid, phosphatidylserine, phosphatidylcholine, phosphatidylethanolamine, phosphatidylinositol, phosphatidylglycerol, sphingomyelin and sphingolipids. It is well-known by the skilled person that these phospholipids are metabolized into lysophospholipids in a living body (see, for example, E. J. Goetzl, S. An, FASEB J. 12, 1589 (1998), Xie Y, and Meier K E. Cell Signal. 2004 Sep; 16(9):975-81).

Examples of the derivative of the lysophospholipid include lysophospholipids modified for improved stability in the blood, such as a lysophospholipid modified with a polyethylene glycol (PEG) derivative (a PEGylated lysophospholipid), a lysophospholipid modified with a water-soluble polymer such as a polyglycerol, and a lysophospholipid modified with any given substituent. Examples of the derivative of the lysophospholipid precursor include a lysophospholipid precursor modified with a PEG derivative, a lysophospholipid precursor modified with a water-soluble polymer, and a lysophospholipid precursor modified with any given substituent. The lysophospholipid, the lysophospholipid precursor or the derivative thereof maybe in the form of a salt. The salt may be a physiologically acceptable salt. Examples of the physiologically acceptable salt include salts with acids such as hydrochloric acid, sulfuric acid, lactic acid, tartaric acid, maleic acid, fumaric acid, oxalic acid, malic acid, citric acid, oleic acid, palmitic acid, nitric acid, phosphoric acid, trifluoroacetic acid, methanesulfonic acid, benzenesulfonic acid and p-toluenesulfonic acid; salts with hydroxides or carbonates of an alkali metal such as sodium and potassium, salts with hydroxides or carbonates of an alkaline earth metal such as calcium, and salts with aluminum hydroxide or carbonate; and salts with triethylamine, benzylamine, diethanolamine, t-butylamine, dicyclohexylamine, arginine, etc.

The lysophospholipid, the lysophospholipid precursor or the derivative thereof can be obtained by known methods, including, for example, (1) chemical synthesis, (2) purification from a biological sample, and (3) enzymatic synthesis. The lysophospholipid, the lysophospholipid precursor or the derivative thereof may be a commercially available product. In the case of chemical synthesis, the lysophospholipid, the lysophospholipid precursor or the derivative thereof maybe produced by an appropriately modified and/or combined method based on the methods described in, for example, Comprehensive Organic Transformations: A Guide to Functional Group Preparations, 2nd Edition (Richard C. Larock, John Wiley & Sons Inc, 1999). In the case of purification from a biological sample, the lysophospholipid, the lysophospholipid precursor or the derivative thereof may be produced by, for example, obtaining fractions from a biological sample by gel filtration or other means and purifying the fractions by silica gel chromatography or reverse-phase column chromatography. In the case of enzymatic synthesis, the lysophospholipid, the lysophospholipid precursor or the derivative thereof may be produced with use of, for example, myeloperoxidase, oxidases, 12/15-lipoxygenase or P450 metabolic enzymes.

Leukocytes include lymphocytes (T cells, B cells, NK cells and NKT cells), monocytes (macrophages and dendritic cells) and granulocytes (neutrophils, eosinophils and basophils). The type of leukocytes whose infiltration into a tumor is induced or promoted by the agent of the present invention is not particularly limited, and the agent of the present invention induces or promotes the infiltration of all types of cells included in the leukocytes as described above. In some embodiments, the leukocytes maybe cells serving to stimulate antitumor immunity in tumors (antitumor immune cells). Examples of such cells include cytotoxic T cells, NK cells, NKT cells, killer cells, macrophages, granulocytes, helper T cells and LAK cells. In some embodiments, the leukocytes whose infiltration into the central part of a tumor is promoted by the agent of the present invention may be CD4-positive cells and/or CD8-positive cells. The CD4-positive cells may be helper T cells, and the CD8-positive cells may be cytotoxic T cells. The type of cells that have infiltrated into a tumor can be examined by, for example, preparing tissue specimens of the tumor and immunostaining the tissue specimens with an antibody against a surface antigen specific to each type of cells.

A tumor is a mass of abnormally growing cells and includes a benign tumor and a malignant tumor. The tumor into which the infiltration of leukocytes is promoted by the agent of the present invention may be a benign tumor or a malignant tumor. In some embodiments, the tumor may be a solid cancer. In solid cancers, blood vessels are tortuous and irregularly branched, the luminal surface is irregular, and vascular permeability is excessively increased. Solid cancers include, but are not limited to, lung cancer, colon cancer, prostate cancer, breast cancer, pancreatic cancer, esophageal cancer, gastric cancer, liver cancer, biliary cancer, spleen cancer, renal cancer, bladder cancer, uterine cancer, ovarian cancer, testicular cancer, thyroid cancer and brain tumor. Solid cancers also include a tumor formed from cancerous blood cells.

The agent of the present invention can be embodied in the form of a medicament. That is, the agent of the present invention can be produced in a dosage form by blending the lysophospholipid receptor-activating substance as an active ingredient with a pharmaceutically acceptable carrier or additive as appropriate according to a known production method for pharmaceutical preparations (e.g., the methods described in the Japanese Pharmacopoeia, etc.). Specifically, the agent of the present invention may be, for example, an oral preparation or a parenteral preparation, including tablets (including sugar-coated tablets, film-coated tablets, sublingual tablets, orally disintegrating tablets, and buccal tablets), pills, powders, granules, capsules (including soft capsules and microcapsules), troches, syrups, liquids, emulsions, suspensions, controlled-release preparations (e.g., fast-release preparations, sustained release preparations, sustained release microcapsules, etc.), aerosols, films (e.g., orally disintegrating films, oral mucosal adhesive films, etc.), injections (e.g., subcutaneous injections, intravenous injections, intramuscular injections, intraperitoneal injections, etc.), intravenous infusions, transdermal preparations, ointments, lotions, patches, suppositories (e.g., rectal suppositories, vaginal suppositories, etc.), pellets, transnasal preparations, transpulmonary preparations (inhalants), and eye drops. The amount of the carrier or the additive to be added is determined as appropriate based on the range of amount conventionally used in the pharmaceutical field. The carrier or the additive that can be added is not particularly limited, and examples include various carriers such as water, physiological saline, other aqueous solvents, and aqueous or oily bases; and various additives such as fillers, binders, pH adjusters, disintegrants, absorption enhancers, lubricants, colorants, corrigents and flavors.

Examples of the additive that can be blended into tablets, capsules and the like include binders such as gelatin, cornstarch, tragacanth and gum arabic; fillers such as crystalline cellulose; bulking agents such as cornstarch, gelatin and alginic acid; lubricants such as magnesium stearate; sweeteners such as sucrose, lactose and saccharin; and flavors such as peppermint, Gaultheria adenothrix oil and cherry. In the case where the unit dosage form is a capsule, a liquid carrier such as fats and oils can be further contained in addition to the above-mentioned ingredients. A sterile composition for injection can be prepared according to the usual procedure for pharmaceutical formulation, for example, by dissolving or suspending an active ingredient in a solvent such as water for injection and a natural vegetable oil. As an aqueous liquid for injection, for example, physiological saline, an isotonic solution containing glucose and an auxiliary substance (e.g., D-sorbitol, D-mannitol, sodium chloride, etc.), or the like can be used, optionally together with a suitable solubilizer such as alcohols (e.g., ethanol etc.), polyalcohols (e.g., propylene glycol, polyethylene glycol, etc.) and nonionic surfactants (e.g., polysorbate 80™, HCO-50, etc.). As an oily liquid, for example, sesame oil, soybean oil, or the like can be used, optionally together with a solubilizer such as benzyl benzoate and benzyl alcohol. Further, an oily liquid, a buffering agent (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant and/or the like may also be added.

The lysophospholipid or a precursor thereof, which is an active ingredient of the agent of the present invention, is a substance found in a living body. Therefore, the agent of the present invention is less toxic to and can be safely administered to humans and other mammals (e.g., rats, mice, rabbits, sheep, pigs, cattle, cats, dogs, monkeys, etc.).

The amount of the active ingredient contained in pharmaceutical preparations is determined as appropriate for the dosage form, the administration method, the carrier and the like. When the active ingredient is a lysophospholipid or a derivative thereof, the amount of the active ingredient can usually be 0.01 to 100% (w/w) relative to the total weight of the pharmaceutical preparation. The amount of the active ingredient may be 0.1 to 95% (w/w) relative to the total weight of the pharmaceutical preparation.

The dose of the active ingredient may vary depending on the subject, the symptoms, the administration route and the like, but in general, the daily oral dose for a human weighing about 60 kg may be, for example, about 0.01 to 1000 mg, about 0.1 to 100 mg, or about 0.5 to 50 mg. The single dose for parenteral administration may also vary depending on patient's condition, the symptoms, the administration method and the like, but for example in the case of intravenous injection, the dose may usually be, for example, about 0.01 to 100 mg, about 0.01 to 50 mg, or about 0.01 to 20 mg per kg of body weight. The total daily dose may be given as a single dose or in divided doses.

The agent of the present invention is able to normalize blood vessels in a tumor in a few hours after administration and to thereby induce or promote infiltration of leukocytes into the whole or partial region of the tumor, thus stimulating antitumor immunity in the tumor. Due to these effects, when the agent of the present invention is used in combination with cancer immunotherapy, the cancer immunotherapy can be enhanced and tumor cytotoxicity can be increased. The phrase "the agent of the present invention is used in combination with cancer immunotherapy" means that the agent of the present invention is administered to a cancer patient receiving cancer immunotherapy or that the agent of the present invention is used in combination with a drug for cancer immunotherapy. When the agent of the present invention is used in combination with cancer immunotherapy, the dosage of the drug for cancer immunotherapy can be reduced, which may lead to reduced side effects. Moreover, the reduction in the dosage of the drug for cancer immunotherapy meets social needs including healthcare cost reduction.

Examples of the cancer immunotherapy include cancer vaccine therapy, immune cell infusion therapy, a therapy for reversal of immunosuppression and a therapy for inducing the depletion of regulatory T cells. In some embodiments, the cancer immunotherapy may be a therapy for reversal of immunosuppression. The immune checkpoint inhibitor used in the therapy for reversal of immunosuppression is an anti-CTLA-4 antibody, a PD-1 blocker, an anti-PD-1 antibody, a PD-L1 blocker, an anti-PD-L1 antibody, or the like. Examples of the immune cell infusion therapy include chimeric antigen receptor-modified T-cell therapy. The administration of the agent of the present invention after depletion of regulatory T cells is expected to produce the same effect as produced by a combination of the agent of the present invention with an immune checkpoint inhibitor because regulatory T cells play a role in immunological tolerance. Examples of the drug that induces the depletion of regulatory T cells include alkylating agents, an IL-2-diphtheria toxin fusion protein, an anti-CD25 antibody, an anti-KIR antibody, an IDO inhibitor and a BRAF inhibitor.

Examples of the drug for cancer immunotherapy include Picibanil, Krestin, sizofiran, lentinan, ubenimex, interferons, interleukins, macrophage colony-stimulating factor, granulocyte colony-stimulating factor, erythropoietin, lymphotoxins, BCG vaccine, Corynebacteriumparvum, levamisole, polysaccharide K, procodazole, ipilimumab, nivolumab, ramucirumab, ofatumumab, panitumumab, pembrolizumab, obinutuzumab, trastuzumab emtansine, tocilizumab, bevacizumab, trastuzumab, siltuximab, cetuximab, infliximab, rituximab and metformin.

When the lysophospholipid or a precursor thereof, which is an active ingredient of the agent of the present invention, is used in combination with cancer vaccine, efficient infiltration of cancer vaccine-stimulated T cells into a tumor can be achieved. In addition, the agent of the present invention can enhance the efficacy of immune cell infusion therapy using immune cells such as T cells from a patient or a non-patient.

As described above, a combined use of the agent of the present invention with cancer immunotherapy can enhance cancer immunotherapy and increase tumor cytotoxicity. Based on this, the agent of the present invention according to an embodiment where the agent is used in combination with cancer immunotherapy can be called an agent for enhancing cancer immunotherapy. Therefore, the present invention includes "an agent for enhancing cancer immunotherapy, comprising a lysophospholipid receptor-activating substance as an active ingredient, the agent being capable of inducing or promoting infiltration of leukocytes into the whole or partial region of a tumor, the agent being used in combination with cancer immunotherapy".

The agent of the present invention can be used in combination with an anticancer drug other than those described above. When an anticancer drug is combined with the agent of the present invention that has stimulatory effect on antitumor immunity, the original anticancer effect of the anticancer drug can be enhanced. Thus, the dosage of the anticancer drug can be reduced, which may lead to reduced side effects. Moreover, the reduction in the dosage of the anticancer drug meets social needs including healthcare cost reduction.

The anticancer drug is not particularly limited and may be, for example, a chemotherapeutic drug or a hormone therapy drug. These anticancer drugs may be in the form of a liposomal formulation. These anticancer drugs may be in the form of a nucleic acid formulation or an antibody formulation.

The chemotherapeutic drug is not particularly limited and examples include alkylating agents such as nitrogen mustard, nitrogen mustard N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylenemelamine, carmustine, lomustine, streptozocin, pipobroman, ethoglucid, carboplatin, cisplatin, miboplatin, nedaplatin, oxaliplatin, altretamine, ambamustine, dibrospidium chloride, fotemustine, prednimustine, pumitepa, Ribomustin, temozolomide, treosulfan, trofosfamide, zinostatin stimalamer, adozelesin, cystemustine and bizelesin; antimetabolites such as mercaptopurine, 6-mercaptopurine riboside, thioinosine, methotrexate, pemetrexed, enocitabine, cytarabine, cytarabine ocfosfate, ancitabine hydrochloride, 5-FU and its derivatives (e.g., fluorouracil, tegafur, UFT, doxifluridine, carmofur, galocitabine, emitefur, capecitabine, etc.), aminopterin, nelzarabine, leucovorin calcium, Tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine and bendamustine; anticancer antibiotics such as actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride and idarubicin hydrochloride; and plant-derived anticancer drugs such as etoposide, etoposide phosphate, vinblastine sulfate, vincristine sulfate, vindesine sulfate, teniposide, paclitaxel, docetaxel, vinorelbine, irinotecan, and irinotecan hydrochloride.

The hormone therapy drug is not particularly limited and examples include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g., tamoxifen citrate, toremifene citrate, etc.), birth-control pills, mepitiostane, testololactone, aminoglutethimide, LH-RH agonists (e.g., goserelin acetate, buserelin, leuprorelin, etc.), droloxifene, epitiostanol, ethinylestradiol sulfonate, aromatase inhibitors (e.g., fadrozole hydrochloride, anastrozole, letrozole, exemestane, vorozole, formestane, etc.), antiandrogens (e.g., flutamide, bicalutamide, nilutamide, etc.), 5α-reductase inhibitors (e.g., finasteride, episteride, etc.), corticosteroids (e.g., dexamethasone, prednisolone, betamethasone, triamcinolone, etc.) and androgen synthesis inhibitors (e.g., abiraterone, etc.).

In the case where the agent of the present invention is used in combination with the drug for cancer immunotherapy or another anticancer drug, they may be simultaneously administered to a subject or separately administered thereto at some interval. The term "used in combination" herein means that the period of treatment with one drug overlaps with the period(s) of treatment with another or other drugs, and the two or more types of drugs are not necessarily required to be simultaneously administered. The mode of combination of the drugs is not particularly limited, and one or more agents of the present invention may be combined with one or more drugs for cancer immunotherapy or one or more other anticancer drugs in any manner. The dose of the drug for cancer immunotherapy or another anticancer drug can be determined based on the clinical dosage of each drug and is appropriately selected depending on the subject, the age and body weight of the subject, the symptoms, the administration time, the dosage form, the administration method, the combination of the drugs, etc.

The present invention further includes the following.

A method for promoting infiltration of leukocytes into the whole region of a tumor, comprising administering a lysophospholipid receptor-activating substance to a mammal.

A lysophospholipid receptor-activating substance for use in promoting infiltration of leukocytes into the whole region of a tumor.

Use of a lysophospholipid receptor-activating substance for production of a leukocyte infiltration promoting agent which promotes infiltration of leukocytes into the whole region of a tumor.

A method for stimulating antitumor immunity, comprising administering a lysophospholipid receptor-activating substance to a mammal.

A lysophospholipid receptor-activating substance for use in stimulating antitumor immunity.

Use of a lysophospholipid receptor-activating substance for production of an antitumor immunostimulatory agent.

A cancer therapeutic agent comprising a lysophospholipid receptor-activating substance as an active ingredient.

A method for treating cancer, comprising administering a lysophospholipid receptor-activating substance to a mammal.

A lysophospholipid receptor-activating substance for use in cancer therapy.

Use of a lysophospholipid receptor-activating substance for production of a cancer therapeutic agent.

A method for enhancing cancer immunotherapy, comprising administering a lysophospholipid receptor-activating substance to a cancer patient receiving cancer immunotherapy.

A lysophospholipid receptor-activating substance for use in enhancing cancer immunotherapy.

Use of a lysophospholipid receptor-activating substance for production of an agent for enhancing cancer immunotherapy.

EXAMPLES

Hereinafter, the present invention will be described in more detail by Reference Examples and Examples, but the present invention is not limited thereto. The sign "%" refers to a percent by mass unless otherwise specified.

Reference Example 1: Structural Changes in Tumor Blood Vessels after Administration of Lysophosphatidic Acid (LPA)

LPA or an LPA derivative was administered to tumor-bearing mice generated by subcutaneous inoculation of a mouse cancer cell line, and post-administration structural changes in tumor blood vessels were examined.

(1) Experimental Method

Lewis lung cancer cells (hereinafter called LLC cells) were used as the mouse cancer cell line. LLC cells ($1 \times 10^6$ cells in 100 μL PBS per animal) were subcutaneously injected into C57BL/6 NCrSlc mice aged 8 weeks (females, SLC, Inc.).

The LPA used was 18:1 LPA (Avanti Polar Lipids, Inc.). The LPA derivative used was VPC31144S (N-{(1S)-2-hydroxy-1-[(phosphonooxy)methyl]ethyl} (9Z) octade c-9-enamide). A 10 mM LPA stock solution and a 10 mM VPC31144S stock solution were separately prepared using 50% ethanol and stored at −30° C. Before use, each of the frozen stock solutions was thawed and homogenized with an ultrasonic cleaner (SND Co., Ltd.) for 1 minute. The solution was diluted in PBS to an appropriate concentration for administration at a dose of 3 mg/kg in 100 μL PBS.

On day 9 post-inoculation, LLC-bearing mice that had developed a tumor with a volume of 60 to 80 mm³ (volume=length×width×height×0.5) were selected and subjected to the experiment. The mice were assigned to three groups: a control group, an LPA group and a VPC31144S group. Each group consisted of three mice. After grouping, LPA and VPC31144S were intraperitoneally administered to the mice of the LPA and VPC31144S groups at a dose of 3 mg/kg/100 μL, respectively. For the control group, 100 μL of PBS was intraperitoneally administered to the mice. The administration was performed once daily for consecutive five days. The tumors were harvested from the mice at 6 days after the start of the administration. The tumors were immersed in 4% paraformaldehyde (PFA)/PBS and shaken at 4° C. overnight for fixation. After fixation, the tumors were washed with cold PBS (4° C.) for 6 hours, during which PBS was replaced with a fresh one every 30 minutes. The tumors were immersed in 15% sucrose/PBS and shaken at 4° C. for 3 hours. The tumors were then immersed in 30% sucrose/PBS and shaken at 4° C. for 3 hours. The tumors were embedded in O.C.T. compound (Tissue-Tek) and frozen at −80° C. for 3 days or longer.

The tumors embedded in O.C.T. compound were sectioned at 40 μm with a cryostat (Leica). The sections were placed on glass slides and air-dried for 2 hours with a dryer. The sections were encircled with a liquid blocker. The glass slides were placed in a slide staining tray and washed with PBS at room temperature for 10 minutes to remove O.C.T. compound. The sections were post-fixed in 4% PFA/PBS at room temperature for 10 minutes and washed with PBS at room temperature for 10 minutes. A blocking solution (5% normal goat serum, 1% BSA and 2% skim milk in PBS) was applied dropwise to the sections, and the sections were blocked at room temperature for 20 minutes. As a primary antibody, Purified Hamster Anti-PECAM-1 Antibody (MAB1398Z, Millipore), which is an anti-mouse CD31 antibody, was diluted to 200-fold in the blocking solution, and the diluted antibody was applied dropwise to the sections. The sections were incubated at 4° C. overnight. The sections were washed five times with PBS containing Tween 20 (PBST) for 10 minutes each and further with PBS for 10 minutes. Alexa Fluor 488 Goat Anti-Hamster IgG (Jackson ImmunoResearch Laboratories) as a secondary antibody was diluted to 400-fold in the blocking solution, and the diluted antibody was applied dropwise to the sections. The sections were incubated in a light-shielding condition for 2 hours. The sections were washed five times with PBST for 10 minutes each. Several drops of Vectashield (Vector Laboratories Inc.) were applied to the sections and the sections were covered with glass coverslips. The immunostained specimens were observed and photographed under a confocal laser microscope (Leica).

(2) Results

Figure 1B:
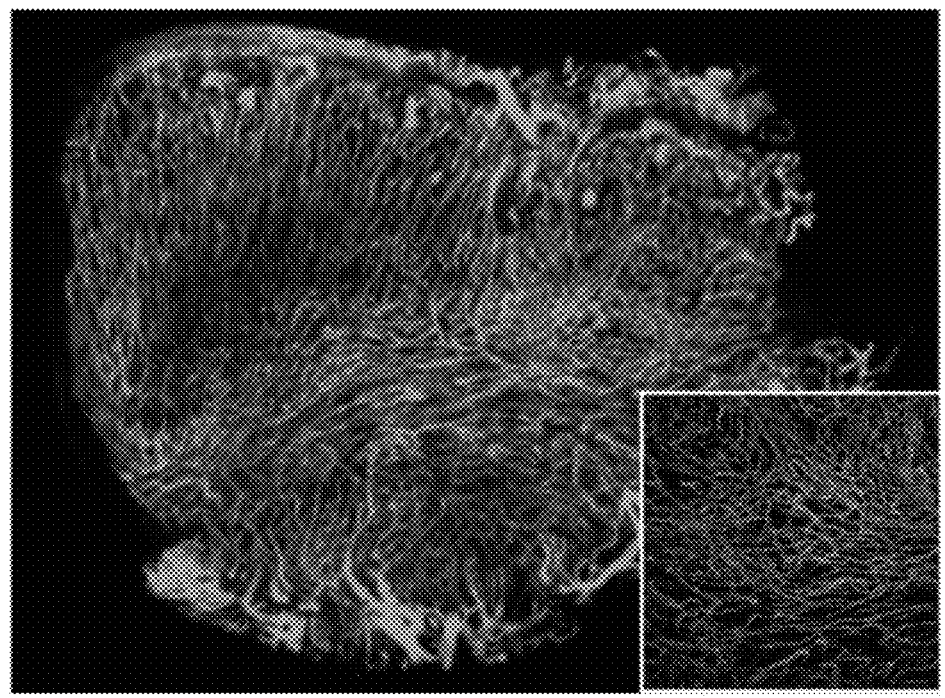

The results are shown in FIGS. 1A and 1B. FIG. 1A is a representative image for the control group, and FIG. 1B is a representative image for the LPA group. In the lower-right box of each image, an enlarged image of the central part of the tumor is shown. Vascular endothelial cells are stained in fluorescent green and visualized in white in each image. FIG. 1A shows a sparse network structure and discontinuity of blood vessels in the central part of the tumor. FIG. 1B shows a continuous network structure of blood vessels. Although the data are not shown, in the VPC31144S group, a continuous network of blood vessels was formed as with the LPA group. Similar results were obtained in experiments using cancer cell lines other than LLC cells, including Colon-26 colorectal cancer cells and 816 melanoma cells.

Reference Example 2: Structural Changes in Tumor Blood Vessels after Administration of Sphingosine-1-phosphate (S1P)

S1P, a lysophospholipid other than LPA, was examined for the ability to induce vascular network formation in the tumor as with LPA.

(1) Experimental Method

LLC cells were subcutaneously inoculated into C57BL/6 NCrSlc mice aged 8 weeks (females, SLC, Inc.) in the same manner as in Reference Example 1. S1P (Avanti Polar Lipids, Inc.) was dissolved in PBS at 10 mM, and the solution was stored at −30° C. as a stock solution. Before use, the frozen stock solution was thawed and homogenized with an ultrasonic cleaner (SND Co., Ltd.) for 1 minute. The S1P solution was diluted in PBS to an appropriate concentration for administration at a dose of 0.3 mg/kg in 100 gL PBS.

LLC-bearing mice on day 9 post-inoculation (animals with a tumor volume of 60 to 80 mm$^3$) were subjected to the experiment. The mice were divided into two groups: a control group and an S1P group (n=3 per group). After grouping, S1P was administered via the tail vein to the mice of the S1P group at a dose of 0.3 mg/kg in 100 µL PBS once daily for consecutive three days including the day of grouping. For the control group, PBS (100 µL) was administered via the tail vein to the mice instead of S1P. At 24 hours after the final administration, the tumors were harvested from the mice, and specimens of tumor blood vessels were prepared in the same manner as in Reference Example 1. The prepared specimens were observed and photographed under a confocal laser microscope (Leica).

(2) Results

Figure 2A:
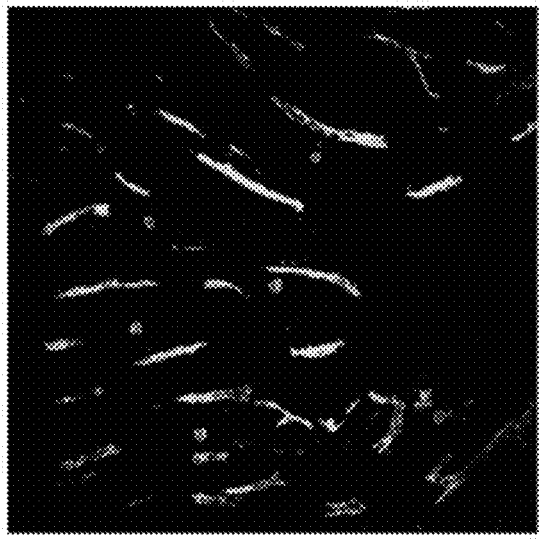
FIGS. 2A and 2B show the structural changes in tumor blood vessels in LLC tumor-bearing mice after administration of sphingosine-1-phosphate (S1P).
Figure 2B:
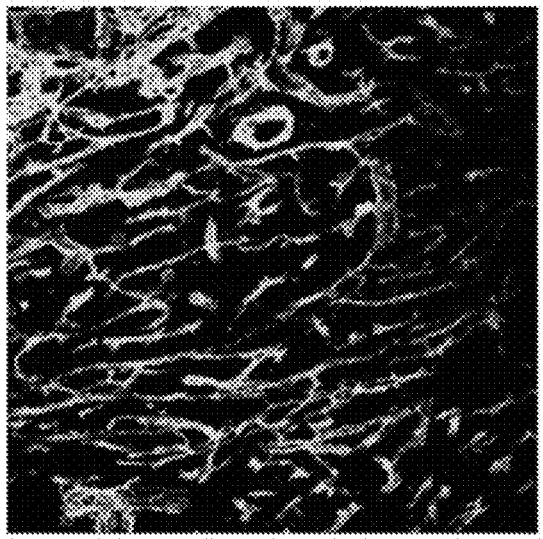

The results are shown in FIGS. 2A and 2B. FIG. 2A is a representative image for the control group, and FIG. 2B is a representative image for the S1P group. As in the case of the administration of LPA, the administration of S1P induced vascular network formation in the tumor. The results revealed that not only LPA but also the different type of lysophospholipid is effective for inducing vascular network formation in the tumor and thereby normalizing the tumor blood vessels.

Reference Example 3: Structural Changes in Lumina of Tumor Blood Vessels after LPA Administration (1) Experimental Method LLC cells were subcutaneously inoculated into C57BL/6 NCrSlc mice aged 8 weeks (females, SLC, Inc.) in the same manner as in Reference Example 1. An LPA solution for administration was prepared in the same manner as in Reference Example 1. LLC-bearing mice on day 9 post-inoculation (animals with a tumor volume of 60 to 80 mm$^3$) were subjected to the experiment. The mice were divided into two groups: a control group and an LPA group (n=3 per group). After grouping, LPA (3 mg/kg/100 µL) or PBS (100 µL) was intraperitoneally administered to the mice. At 24 hours after LPA or PBS administration, the mice were fixed by perfusion with a fixative under anesthesia with pentobarbital (Kyoritsu Seiyaku Corporation). The fixative used was 0.1 M phosphate buffer (pH 7.4) containing 2% formaldehyde and 2.5% glutaraldehyde. After the fixation by perfusion, the tumors were harvested, immersed in the same fixative as used for perfusion, and shaken at 4° C. overnight. The tumors were further immersed in 0.1 M phosphate buffer (pH 7.4) containing 1% osmium tetroxide and 0.5% potassium ferrocyanide for fixation. The tumors were dehydrated in an ascending series of ethanol, then the alcohol was replaced with t-butyl alcohol, and the tumors were freeze-dried. After freeze-drying, osmium tetroxide was applied to the tumors by vapor deposition, and the luminal surface of the blood vessels was observed in an S-4800 scanning electron microscope (Hitachi High-Technologies Corporation).

(2) Results

Figure 3A:
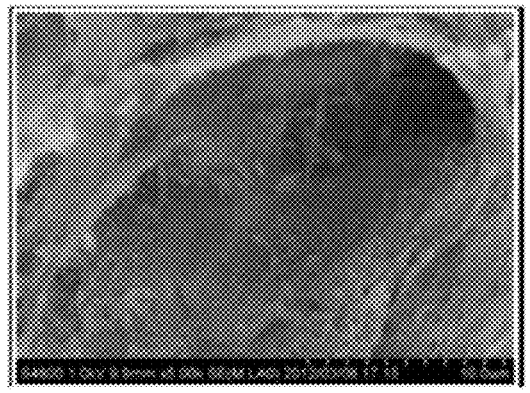
FIGS. 3A and 3B show the structural changes in the lumen of a tumor blood vessel in LLC tumor-bearing mice after administration of lysophosphatidic acid (LPA).
Figure 3B:
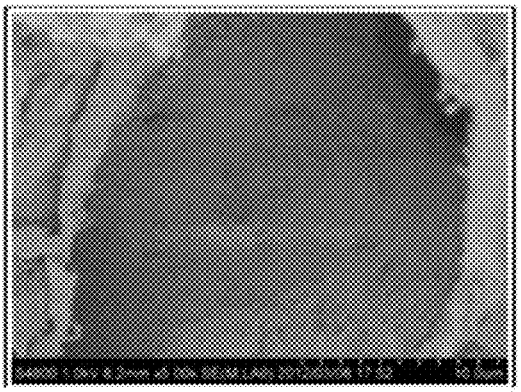

The results are shown in FIGS. 3A and 3B. FIG. 3A is a representative image for the control group, and FIG. 3B is a representative image for the LPA group. The blood vessels in the control group had a rough luminal surface with filopodial protrusion, but the blood vessels in the LPA group had a very smooth luminal surface. The results indicate that LPA administration potentially improves blood circulation in tumors.

Reference Example 4: Improvement of Drug Delivery from Tumor Blood Vessels to Tumor Tissues after LPA Administration As is commonly known, low blood flow and vascular hyperpermeability are the hallmarks of tumors. These cause an increase in tumor interstitial fluid pressure, leading to no difference in osmotic pressure between the tumor parenchyma and the blood vessels. This condition is a great obstacle to substance penetration from the vascular lumen to tumor tissues. Based on the above results showing that LPA administration induces a dense network formation of tumor blood vessels with a smooth luminal surface, it was hypothesized that LPA administration would improve drug penetration from tumor blood vessels. To examine drug penetration into tumors after LPA administration, the following experiments were conducted.

(1) Experimental Method

LLC cells were subcutaneously inoculated into C57BL/6 NCrSlc mice aged 8 weeks (females, SLC, Inc.) in the same manner as in Reference Example 1. An LPA solution for administration was prepared in the same manner as in Reference Example 1. On day 11 post-inoculation, LLC-bearing mice that had developed a tumor with a volume of 100 to 120 mm$^3$ were selected. The mice were divided into two groups: a control group and an LPA group (n=3 per group). After grouping, LPA (3 mg/kg/100 µL) or PBS (100 µL) was intraperitoneally administered to the mice. At 24 hours after LPA or PBS administration, doxorubicin (doxorubicin hydrochloride, Nippon Kayaku Co., Ltd.) was administered via the tail vein to the mice at a dose of 1.5 mg/kg under pentobarbital anesthesia. The doxorubicin was prepared as a solution by dissolving and diluting doxorubicin hydrochloride in physiological saline (Otsuka Pharmaceutical Co., Ltd.) to an appropriate concentration for administration at a dose of 1.5 mg/kg and homogenizing the solution with an ultrasonic cleaner for 1 minute before administration. Doxorubicin is a fluorescent anticancer drug that can be detected at an excitation wavelength of 480 nm and a measurement wavelength of 575 nm. At 20 minutes after the administration of doxorubicin, the tumors were harvested from the mice, and tumor specimens were prepared in the same manner as in Example 1 except that the thickness of the sections was 20 µm. The prepared sections were observed and photographed under a confocal laser microscope (Leica).

(2) Results

The results are shown in FIGS. 4A and 4B. FIG. 4A is a representative image for the control group, and FIG. 4B is a representative image for the LPA group. In FIGS. 4A and 4B, the arrows indicate red fluorescent signals of doxorubicin. Vascular endothelial cells are shown in fluorescent green due to binding to anti-CD31 antibody. In the control group, the penetration of doxorubicin into tumors was hardly observed, but in the LPA administration group, the delivery of doxorubicin from tumor blood vessels to the deep part of the tumor was observed.

Example 1: Changes in Localization of Immune Cells in Tumor by LPA Administration LPA was administered to tumor-bearing mice generated by subcutaneous inoculation of a mouse cancer cell line, and changes in the localization of immune cells in the tumor were examined.

(1) Experimental Method

The tumor sections prepared in Reference Example 1 were immunostained with an anti-CD4 antibody and an anti-CD8 antibody. As a primary antibody, Purified Hamster Anti-PECAM-1 Antibody (Millipore), which is an anti-mouse CD31 antibody, PE-labeled Anti-mouse CD4 Antibody (Pharmingen) or FITC-labeled Anti-mouse CD8 Antibody (Pharmingen) was used. As a secondary antibody, Alexa Fluor 647-conjugated Anti-Armenian Hamster IgG was used. The immunostaining was performed in the same procedure as in Reference Example 1. The immunostained sections were observed and photographed under a confocal laser microscope (Leica).

(2) Results

Figure 5:
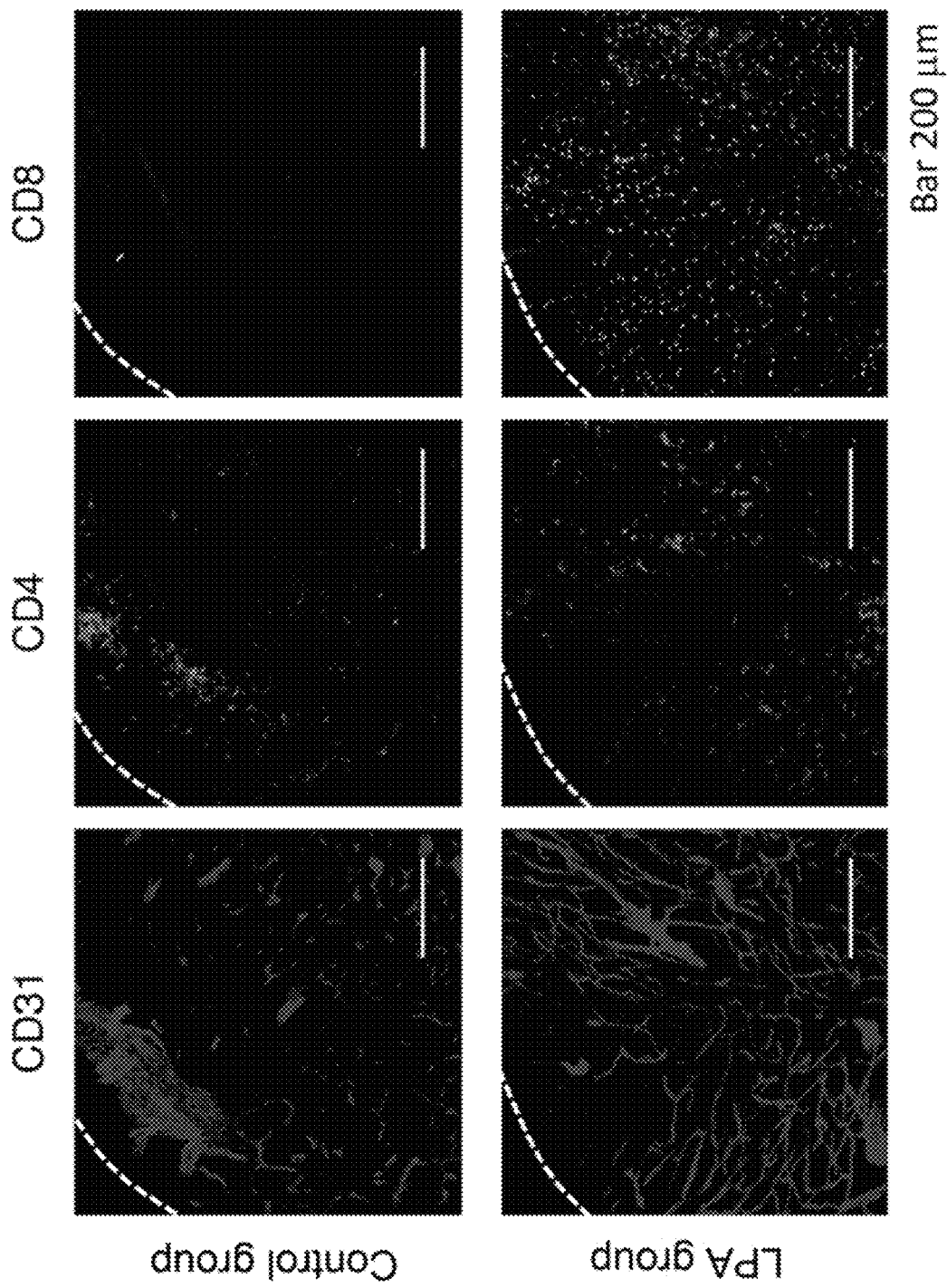
FIG. 5 shows the changes in the localization of immune cells in the tumor in LLC tumor-bearing mice after administration of lysophosphatidic acid (LPA).

The results are shown in FIG. 5. The left panels are images of anti-CD31 antibody staining. Blood vessels are stained in fluorescent blue and visualized in white in each image. The center panels are images of anti-CD4 antibody staining. CD4-positive cells are stained in fluorescent red and visualized in white in each image. The right panels are images of anti-CD8 antibody staining. CD8-positive cells are stained in fluorescent green and visualized in white in each image. The upper panels are images for the control group, and the lower panels are images for the LPA group. The dotted line in each image of FIG. 5 represents the border of the tumor. As is clear from FIG. 5, in the control group, blood vessels were discontinuous (left); a small number of CD4-positive cells were present in the marginal region of the tumor, but no CD4-positive cells were present in the central part (center); and CD8-positive cells were totally absent in the central part and the marginal region (right). In contrast, in the LPA group, blood vessels were continuous (left); CD4-positive cells were present even in the central part of the tumor (center); and CD8-positive cells were present in the whole tumor region (right). The results indicate that LPA administration can improve antitumor immune response in the tumor and create an environment allowing the induction of tumor cell death.

Example 2: Effect of LPA Administration on Subcutaneous Tumor Formed in Mice

For further research based on the above results showing that LPA administration induces infiltration of immune cells into the central part of the tumor, LPA was examined for the ability to inhibit tumor growth.

3-1 Effect on Tumor Formed from LLC Cells (1) Experimental Method

LLC cells ($1\times10^6$ cells in 100 μL PBS per animal) were subcutaneously injected into C57BL/6 NCrSlc mice aged 8 weeks (females) in the same manner as in Reference Example 1. An LPA solution for administration was prepared in the same manner as in Reference Example 1. 5-FU (Kyowa Hakko Kirin Co., Ltd.) was used as an anticancer drug. 5-FU was prepared as a solution in physiological saline (Otsuka Pharmaceutical Co., Ltd.). On day 7 post-inoculation, LLC-bearing mice that had developed a tumor with a volume of 30 to 50 mm$^3$ were selected and subjected to the experiment. The mice were assigned to three groups: a control group, a 5-FU group and an LPA group (n=3 per group). After grouping, LPA (3 mg/kg/100 μL), 5-FU (100 mg/kg/100 μL) or PBS (100 μL) was intraperitoneally administered to the mice. The administration of LPA or PBS was performed once daily for consecutive seven days. The administration of 5-FU was performed once weekly, 2 times in total (day 7 and day 14 post-inoculation). Tumor size was measured over time after the start of the administration. Tumor volume was calculated by the following formula: length×width×height×0.5.

(2) Results

Figure 6:
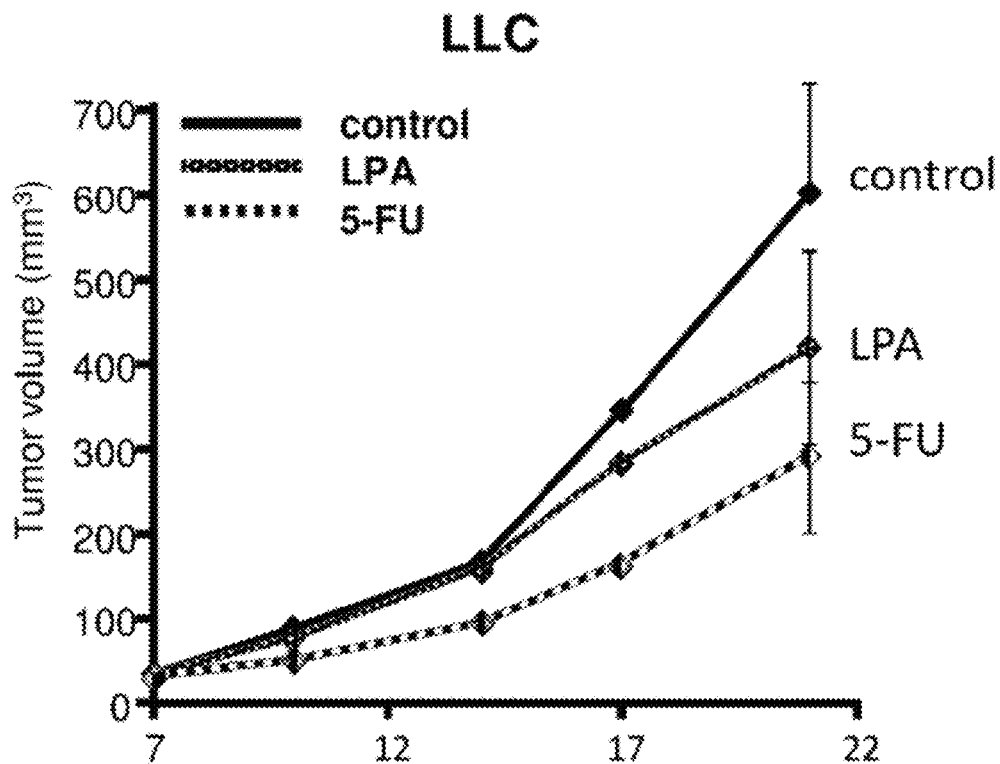
FIG. 6 shows the tumor growth inhibitory effect of lysophosphatidic acid (LPA) administered to LLC tumor-bearing mice.

The results are shown in FIG. 6. As is clear from FIG. 6, in comparison with the control group, the 5-FU group showed a remarkable inhibition of tumor growth, and albeit to a slightly lesser extent, the LPA group also showed inhibition of tumor growth.

3-2 Effect on Tumor Formed from Melanoma Cells (1) Experimental Method

The B16-BL6 mouse melanoma cell line was used. B16-BL6 cells ($1\times10^6$ cells in 100 L PBS per animal) were subcutaneously injected into C57BL/6 NCrSlc mice aged 8 weeks (females). On day 7 post-inoculation, B16-BL6-bearing mice that had developed a tumor with a volume of 30 to 50 mm$^3$ were selected and subjected to the experiment. The subsequent experimental procedure was the same as that described in the above 3-1.

(2) Results

Figure 7:
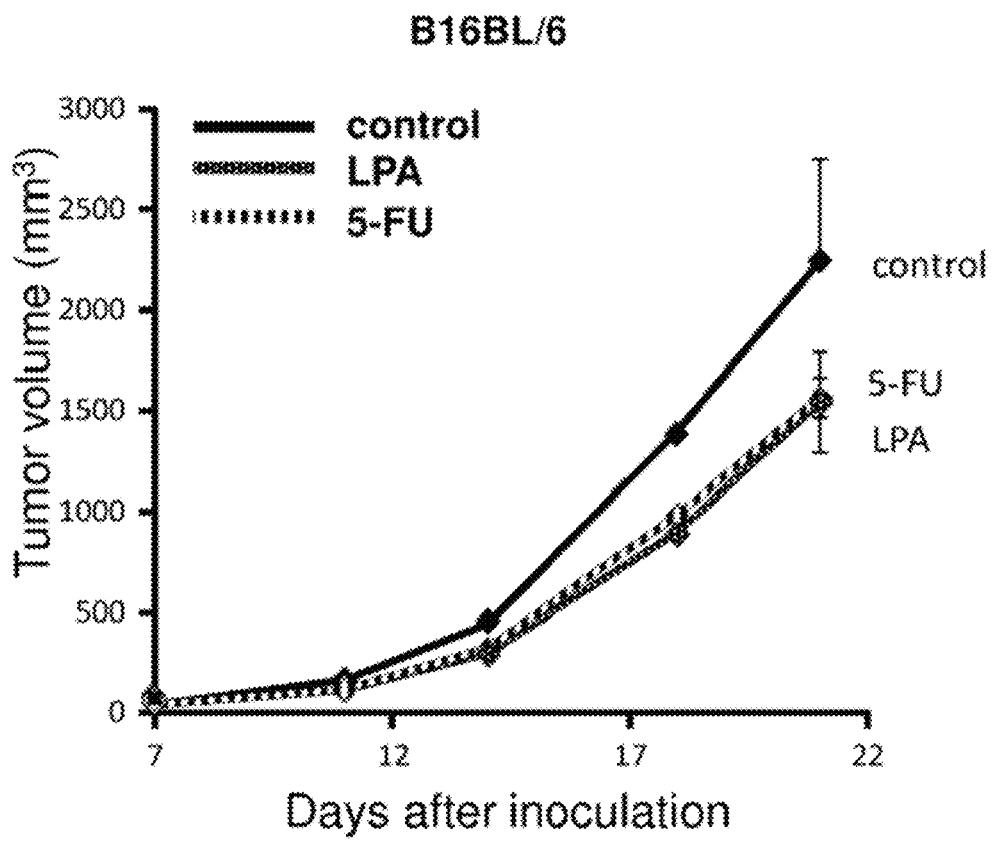
FIG. 7 shows the tumor growth inhibitory effect of lysophosphatidic acid (LPA) administered to B16-BL6 tumor-bearing mice.

The results are shown in FIG. 7. As is clear from FIG. 7, the inhibitory effect of LPA on the growth of the tumor formed from melanoma cells was comparable to that of 5-FU.

LPA neither destroys tumor vessels nor induces hypoxia in cancer and is therefore expected to induce no malignant transformation of cancer cells. The findings of the above Reference Examples and Example demonstrate that LPA is able to promote infiltration of immune cells into the whole tumor region and to thus enhance tumor cell killing by immune cells such as cytotoxic T cells; and that LPA allows CD4-positive immune cells to exert surveillance function in a tumor as with normal tissue. Moreover, LPA causes no damage to blood vessels in normal tissue and therefore has a very low risk of side effects. LPA seems to exert such functions regardless of the type of cancer and is therefore applicable to any type of cancer. Particularly, LPA is expected to exert remarkable effect on cancers characterized by low blood flow (pancreatic cancer etc.).

Example 3: Enhancement of Antitumor Effect by Combined Use of LPA and Immune Checkpoint Inhibitor For further research based on the above results showing that LPA administration induces infiltration of a larger number of immune cells into the tumor, the combined effect of LPA and an immune checkpoint inhibitor was examined.

(1) Experimental Method

LLC cells ($1\times10^6$ cells in 100 μL PBS per animal) were subcutaneously injected into C57BL/6 NCrSlc mice aged 8 weeks (females) in the same manner as in Reference Example 1. On day 6 post-inoculation, LLC-bearing mice that had developed a tumor with a volume of 30 to 40 mm$^3$ (volume=length×width×height×0.5) were selected. The mice were divided into four groups: a control group, an LPA administration group, an anti-PD-1 antibody administration group and an LPA plus anti-PD-1 antibody administration group, and subjected to the experiment. To the LPA administration group and to the LPA plus anti-PD-1 antibody administration group, LPA (3 mg/kg/100 μL) was intraperitoneally administered consecutively from day 6 through day 20 post-inoculation of the tumor cells. In the anti-PD-1 antibody administration group and in the LPA plus anti-PD-1 antibody administration group, anti-PD-1antibody therapy was started from day 7 post-inoculation of the tumor cells. Specifically, an anti-mouse PD-1 antibody (Clone: RMP1-14, BioXcell, BE0146) was intraperitoneally administered at a dose of 100 μg/mouse on day 7, day 9, day 11, day 14, day 16 and day 18 post-inoculation of the tumor cells. To the control group and to the LPA administration group, an isotype control antibody (Clone: 2A3, BioXcell, BE0089) was administered at a dose of 100 μg/mouse following the same schedule as in the administration of the anti-PD-1 antibody. Tumor volume was measured over time until day 21.

(2) Results

Figure 8A:
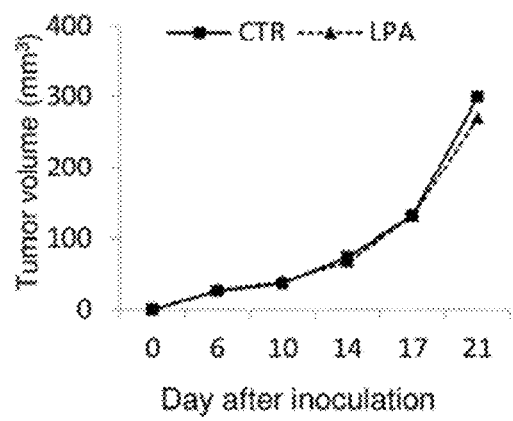
FIGS. 8A, 8B and 8C show the tumor growth inhibitory effect of lysophosphatidic acid (LPA) alone (FIG. 8A), an anti-PD-1 antibody alone (FIG. 8B) or LPA in combination with the anti-PD-1 antibody (FIG. 8C) administered to LLC tumor-bearing mice.
Figure 8B:
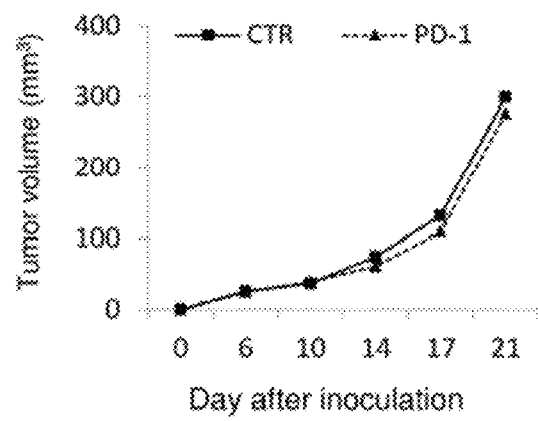
Figure 8C:
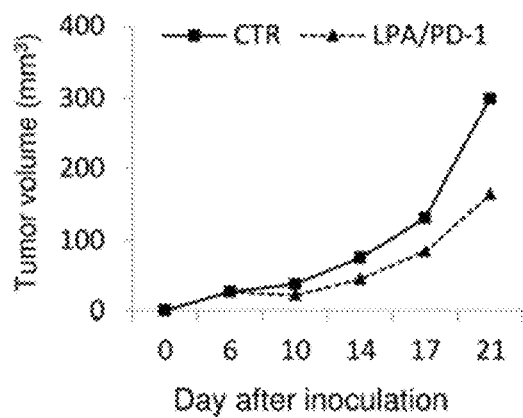

The results are shown in FIGS. 8A, 8B and 8C. FIG. 8A shows the results for the LPA administration group and for the control group. FIG. 8B shows the results for the anti-PD-1 antibody administration group and for the control group. FIG. 8C shows the results for the LPA plus anti-PD-1 antibody administration group and for the control group. As shown by the results of the experiment performed on the administration schedule of Example 3, both the administration of LPA alone (FIG. 8A) and the administration of anti-PD-1 antibody alone (FIG. 8B) slightly inhibited tumor growth in comparison with the control group, but the combined administration of LPA and the anti-PD-1 antibody (FIG. 8C) remarkably inhibited tumor growth in comparison with the control group.

Immune checkpoint inhibitors including anti-PD-1 antibodies are promising antitumor drugs, but recent studies have shown that these drugs are poorly effective when used alone. One possible cause is that immune checkpoint inhibitors, which are capable of inducing lymphocytes' antitumor activity, cannot fully exert such an effect if lymphocytes cannot infiltrate into a tumor. The results of Example 3 demonstrate that LPA enhances infiltration of immune cells from tumor vessels into tumors by activating LPAR4 and thereby allows the immune checkpoint inhibitor used in combination with LPA to fully exert its effect.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for inducing or promoting infiltration of leukocytes into the whole or partial region of a tumor, comprising administering a lysophospholipid receptor-activating substance to a subject receiving cancer immunotherapy, wherein the lysophospholipid receptor-activating substance is a lysophosphatidic acid receptor 4-activating substance with lysophospholipid-like structure.

2. The method according to claim 1, wherein the leukocytes are CD4-positive cells and/or CD8-positive cells.

3. The method according to claim 1, wherein the cancer immunotherapy is a therapy for reversal of immunosuppression.

4. The method according to claim 3, wherein the therapy for reversal of immunosuppression uses an immune checkpoint inhibitor, and wherein the immune checkpoint inhibitor is an anti-CTLA-4 antagonistic antibody, a PD-1 blocker, an anti-PD-1 antagonistic antibody, a PD-L1 blocker or an anti-PD-L1 antagonistic antibody.

5. The method according to claim 4, wherein the immune checkpoint inhibitor is a PD-1 blocker, an anti-PD-1 antagonistic antibody, a PD-L1 blocker or an anti-PD-L1 antagonistic antibody.

6. The method according to claim 5, wherein the immune checkpoint inhibitor is an anti-PD-1 antagonistic antibody.

7. A method for enhancing cancer immunotherapy, comprising administering a lysophospholipid receptor-activating substance to a subject receiving cancer immunotherapy, wherein the lysophospholipid receptor-activating substance is a lysophosphatidic acid receptor 4-activating substance with lysophospholipid-like structure.

8. The method according to claim 7, wherein the cancer immunotherapy is a therapy for reversal of immunosuppression.

9. The method according to claim 8, wherein the therapy for reversal of immunosuppression uses an immune checkpoint inhibitor, and wherein the immune checkpoint inhibitor is an anti-CTLA-4 antagonistic antibody, a PD-1 blocker, an anti-PD-1 antagonistic antibody, a PD-L1 blocker or an anti-PD-L1 antagonistic antibody.

10. The method according to claim 9, wherein the immune checkpoint inhibitor is a PD-1 blocker, an anti-PD-1 antagonistic antibody, a PD-L1 blocker or an anti-PD-L1 antagonistic antibody.

11. The method according to claim 10, wherein the immune checkpoint inhibitor is an anti-PD-1 antagonistic antibody.

12. A method for stimulating antitumor immunity by inducing or promoting infiltration of leukocytes into the whole or partial region of a tumor, comprising administering a lysophospholipid receptor-activating substance to a subject receiving cancer immunotherapy, wherein the lysophospholipid receptor-activating substance is a lysophosphatidic acid receptor 4-activating substance with lysophospholipid-like structure.

13. The method according to claim 12, wherein the leukocytes are CD4-positive cells and/or CD8-positive cells.

* * * * *